United States Patent [19]

Hanson

[11] 4,386,909
[45] Jun. 7, 1983

[54] ORTHODONTIC ARCH WIRES

[75] Inventor: Gustaf H. Hanson, Hamilton, Canada

[73] Assignee: Augusta Developments Inc., Hamilton, Canada

[21] Appl. No.: 367,652

[22] Filed: Apr. 12, 1982

[51] Int. Cl.³ .............................................. A61C 7/00
[52] U.S. Cl. .................................................... 433/20
[58] Field of Search .......................................... 433/20

[56] References Cited

U.S. PATENT DOCUMENTS 2,566,414 9/1951 Henry ................................... 433/20
3,043,007 7/1962 Wallshein ............................ 433/20

Primary Examiner—Robert Peshock
Attorney, Agent, or Firm—Hirons, Rogers & Scott

[57] ABSTRACT

The invention provides an orthodontic arch wire of particular cross-section for use with an orthodontic bracket as disclosed in my earlier patent Ser. No. 3,772,787. This bracket has a mesial-distal extending slot to receive the arch wire, the labial face of which is closed by a sliding U-shaped spring retainer member, one end of which protrudes into the slot to engage the arch wire labial face. The wire cross-section has straight parallel occlusal and gingival sides with the occlusal longer than the gingival. The lingual side is also straight and at right angles to the occlusal and gingival sides. The labial side that is contacted by the retainer member is outwardly convex curved about a radius within the cross-section, the preferred ratio of occlusal side length to radius being from 1:0.4 to 1:0.76.

7 Claims, 5 Drawing Figures

ORTHODONTIC ARCH WIRES

FIELD OF THE INVENTION

The present invention is concerned with improvements in or relating to orthodontic arch wires.

REVIEW OF THE PRIOR ART

An essential part of any orthodontic system is an arch wire, more usually a set of such wires of different characteristics, that connects together the orthodontic brackets attached to the teeth that are to be moved during the orthodontic procedure. One type of arch wire used hitherto is of circular cross-section and passes through a mesial-distal extending slot of rectangular cross-section in each bracket, this slot being open at the labial side of the bracket for insertion of the wire therein. The wire may be a single solid strand or may consist of a plurality of strands woven or twisted together, the orthodontist being provided with a variety of these wires of different diameters and different physical characteristics, so that he can select the one that is most appropriate for the prescribed course of treatment.

Another type of wire is of rectangular cross-section and of dimensions such that it fits with some clearance in the said rectangular mesial-distal extending slot, but cannot rotate in the slot about the mesial-distal direction more than a limited amount without encountering the walls of the slot and thereafter applying a torque to the bracket about the mesial-distal axis and thus to the tooth to which it is attached. Both types of wire can be arranged to apply a rotation to each bracket about a corresponding occlusal-gingival direction (or axis), and to apply a tip to each bracket about a corresponding lingual-labial axis. It is normal practice to use different wires at different stages of a course of orthodontic treatment.

There is described and claimed in my prior U.S. Pat. Ser. Nos. 3,772,787 and 4,248,588, a new orthodontic bracket in which the bracket body is provided with a mesial-distal extending slot which is of rectangular cross-section and open at the labial face. The body is embraced by a generally U-shaped retainer member of flat spring steel that can be slid on the body between a slot-closed position, in which it closes the labial face of the slot to retain the arch wire therein, and a slot-open position in which the arch wire is readily inserted in and removed from the slot. In the form of the bracket disclosed in my U.S. Pat. Ser. No. 4,248,588 the end of the retainer member that closes the slot is arranged to intrude or protrude into the slot and engage the arch wire, so that any displacement of the wire out of the slot causes resilient engagement between the wire and the retainer member, causing the retainer member to apply consequent tip and rotation reaction forces to the wire and thus to the bracket and the tooth to which it is fastened.

DEFINITION OF THE INVENTION

It is an object of the invention to provide a new arch wire particularly suited for use with my orthodontic bracket.

In accordance with the present invention there is provided an orthodontic arch wire for use with an orthodontic bracket of the kind having a mesial-distal extending slot which is of rectangular cross-section perpendicular to the mesial-distal axis, the arch wire having a cross-section perpendicular to its direction of elongation such that the occlusal and gingival sides are straight and parallel to one another with the occlusal side longer than the gingival side, the lingual side is straight and perpendicular to the occlusal and gingival sides, and at least the major part of the labial side is smoothly outwardly-convex curved merging smoothly at one end with the gingival side, and at the other end with any remaining minor part of the labial side.

Preferably the entire labial side is said smoothly outwardly-convex curved merging smoothly at one end with the gingival side, and at the other end with an outwardly convex curved junction between the labial and occlusal sides.

DESCRIPTION OF THE DRAWINGS

Arch wires which are particular preferred embodiments of the invention will now be described, by way of example, with reference to the accompanying diagrammatic drawings, wherein.

DESCRIPTION OF THE PREFERRED EMBODIMENTS

Figure 1:
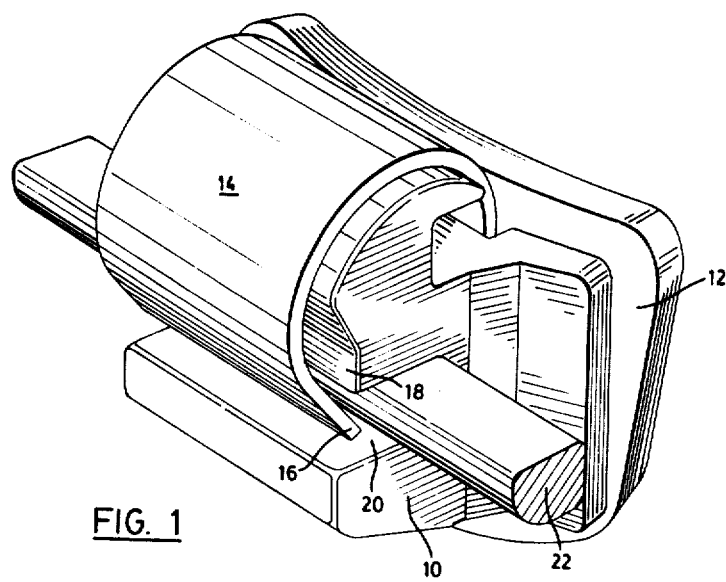
FIG. 1 is a perspective view of an orthodontic bracket as described and claimed in my prior U.S. Pat. Ser. No. 4,248,588 with which the arch wire is to be used.
Figure 2:
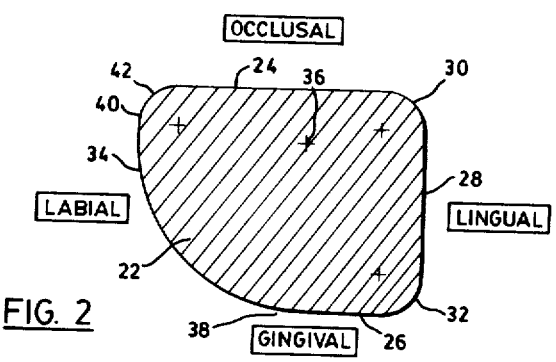
FIG. 2 is a cross-section through an arch wire of the invention.

The orthodontic bracket illustrated by FIG. 1 is described in more detail in my prior U.S. Pat. No. 4,248,588 the disclosure of which is incorporated herein by reference, together with the disclosure of my earlier U.S. Pat. No. 3,772,787.

Such a bracket consists of a stainless steel body 10 fastened in some suitable manner as by laser welding to a pad 12 which is in turn fastened to the tooth by a suitable cement. In some systems the body is fastened to an endless band which encircles the tooth, but this type is not illustrated. A U-shaped retainer member 14, of spring stainless steel strip, is mounted on the body and can be moved by sliding thereon from a slot-open position in which its free edge 16 is engaged on a parking land 18, to a slot-closed position shown in the drawing in which it closes the labial face of a mesio-distal extending, arch-wire-receiving slot 20 with the said free edge 16 protruding into the slot.

An arch wire 22 of the invention engaged in the slot has its labial face engaged by the lingual surface of the portion of the retainer member 14 that intrudes into the slot 20. The cross-section of the arch wire perpendicular to the mesio-distal direction is such that the occlusal side 24 and the gingival side 26 are both straight and parallel to one another, the occlusal side being longer than the gingival side. The lingual side 28 is also straight and is perpendicular to the two sides 24 and 26, the two respective junctions 30 and 32 being outwardly convex curved to provide respective smooth transitions between the sides. The labial side 34 has the major part thereof smoothly outwardly convex curved about a radius centered at point 36 within the cross-section, this major part merging smoothly at one end at about a location 38 with the gingival side 26 and at the other end with a minor straight remaining part 40 that in turn merges smoothly with an outwardly convex junction 42 between itself and the occlusal force 24. It will be seen that in this embodiment the length of the straight minor part 40 is very small as compared to that of the curved part, and in some embodiments the minor part may be non-existent, so that the curved part is the entire side 34 which merges directly with the junction 42.

A typical orthodontic bracket of the invention will have an occlusal-gingival height of 2.5 mm (0.099 inch), a mesial-distal width of 2.2 mm (0.088 inch) and a lingual-labial depth of 1.55 mm (0.061 inch). A typical slot will have an occlusal face of depth 0.7 mm (0.028 inch) and a lingual face of height 0.56 mm (0.022 inch) and the wire intended for use with such a bracket will have an occlusal side 24 of length 0.64 mm (0.025 inch) and a lingual side 28 of length 0.51 mm (0.020 inch). The labial side 34 will have a radius of from 0.25 mm (0.010 inch) to 0.38 mm (0.016 inch), so that the ratio of the length of the straight occlusal wire side to that of the radius of the curvature of the curved labial side is from 0.4 to 0.68. Another typical slot has an occlusal face of depth 0.64 mm (0.025 inch) and a lingual face of height 0.46 mm (0.018 inch), the corresponding wire having an occlusal side 24 of 0.56 mm (0.022 inch) and a lingual side 28 of length 0.43 mm (0.017 inch). The labial side has a radius of from 0.23 mm (0.009 inch) to 0.33 mm (0.013 inch), so that the corresponding ratio is from 0.52 to 0.76. A suitable radius for each of the junctions 30, 32 and 42 is about 0.076 mm (0.003 inch).

Figures 3, 4:
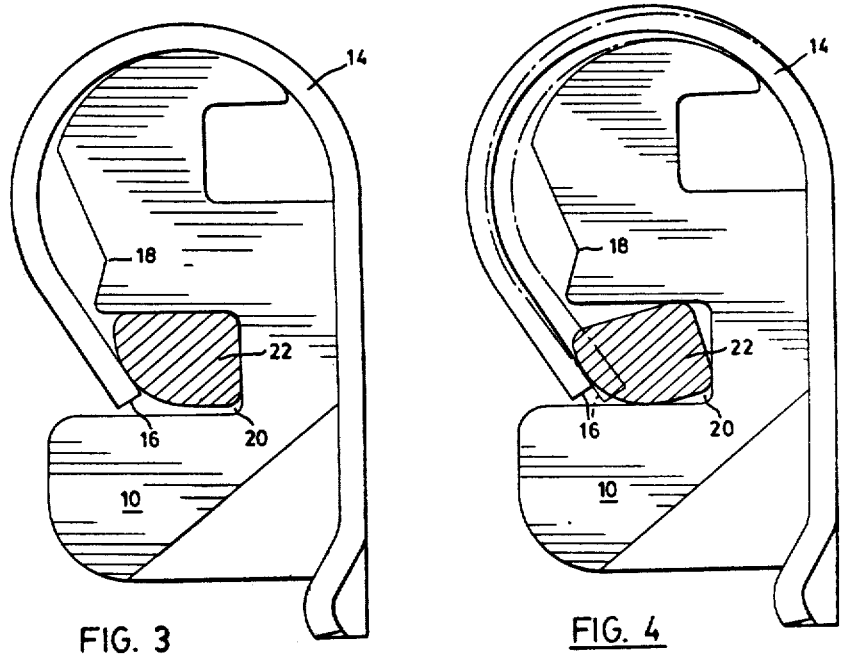
FIGS. 3 and 4 are schematic side-elevations of a bracket to show the manner of cooperation between the bracket and an arch wire of the invention.

It will be seen that the lingual surface of the spring member 14 has an approximately longitudinal engagement with the labial surface of the arch wire allowing a smooth gliding cam action between these two surfaces as the arch wire moves in the slot about the mesial-distal axis. This cam action is mutually advantageous in that the spring member is held more securely in the slot-closed position due to the gingivally-directed force generated on it by the arch wire. FIG. 3 shows the relative orientation of the slot and the wire when the wire is at 0° of rotation therein, while FIG. 4 shows the wire at one extreme of anti-clockwise rotation. Typically the arch wire has about 15° of rotational freedom about this mesio-distal axis, usually about 11° anti-clockwise and about 4° clockwise, before its occlusal and lingual walls are engaged with the corresponding walls of the slot.

The invention permits the use of wires that are substantially smaller than the slot with a member of important consequent advantages. Thus, the manufacturing tolerances of the wires and slots are already extremely small and any relief in this respect is welcomed by the manufacturer. The orthodontist finds it much easier during the procedure to insert an undersized wire in the slot, with increase in speed and comfort to the patient. The spring can act upon the arch wire to urge it and move it in the occlusal direction, which cannot happen when the wire is a close fit in the slot, giving another degree of choice to the orthodontist in the movement to be obtained. The cam action ensures that the wire is held captive with a relatively lighter force so that there is less friction and the bracket can move more easily in the mesial-distal direction along the wire.

Such undersized wires are more effective for producing torque movement than heavy rectangular wires which depend solely on the tightness of fit between themselves and the slot, and energy stored within the wire in the form of elastic torsional strain. They also permit so-called "torquing", that is torque rotation (see FIG. 1) about a slightly-moving mesio-distal axis, by the application of very light forces from the spring member, which forces remain active over a relatively long angle of rotation (e.g. up to about 19°) even with a stiff wire that would otherwise only permit rotation over a small angle before its elastic strain has been eliminated; such a stiff wire is to be preferred since it is more durable in the harsh environment of the human mouth. These easily-inserted, undersized stiff wires are particularly helpful when the orthodontist wishes to apply crown or root torque (which are opposites of one another), namely rotation of the crown or root respectively about a mesio-distal axis running through the arch wire slot such that the occlusal or incisal edges move lingually or labially.

Figure 5:
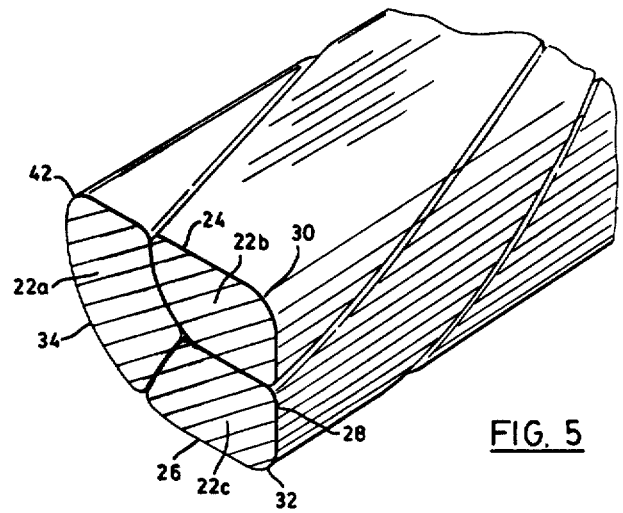
FIG. 5 is a perspective view of a multi-strand wire of the invention.

Although in the embodiment of FIGS. 1-4 a single solid wire is illustrated in other embodiments it can be formed of a bundle of wires laid or twisted together to give a different characteristic, provided that the external envelope of the wire is as specified. An example of such a wire is illustrated in FIG. 5 where three separate strands 22c, 22b and 22c have been rolled together to the required cross-sectional form. More than three strands can of course be employed. Such twisted or braided wires are used when the wire is required to be very flexible to permit it to pass from bracket to bracket e.g. when the alignment (leveling) of the teeth has not yet been completed and the wire must bend substantially between adjacent teeth.

I claim:

1. An orthodontic arch wire for use with an orthodontic bracket of the kind having a mesial-distal extending slot of rectangular cross-section perpendicular to the mesial-distal axis, the arch wire having a cross-section perpendicular to its direction of elongation such that the occlusal and gingival sides are straight and parallel to one another with the occlusal side longer than the gingival side, the lingual side is straight and perpendicular to the occlusal and gingival sides, and at least the major part of the labial side is smoothly outwardly-convex curved merging smoothly at one end with the gingival side, and at the other end with any remaining minor part of the labial side.

2. An orthodontic arch wire as claimed in claim 1, wherein the entire labial side is said smoothly outwardly-convex curved merging smoothly at one end with the gingival side, and at the other end with an outwardly convex curved junction between the labial and occlusal sides.

3. An orthodontic arch wire as claimed in claim 2, wherein the two junctions between the occlusal, lingual and gingival sides are both smoothly outwardly convex curved to provide a smooth transition between the junction-connected sides.

4. An orthodontic arch wire as claimed in claim 1, wherein all of the junctions between the cross-section sides are smoothly outwardly convex curved to provide smooth respective transitions between the junction-connected sides.

5. An orthodontic arch wire as claimed in any one of claims 1 to 4, wherein the ratio between the length of the straight occlusal side and the radius of curvature of the curved labial side is from 1:0.4 to 1:0.76.

6. An orthodontic wire as claimed in any one of claims 1 to 4, wherein the wire occlusal side is of length 0.64 mm (0.025 inch), the lingual side is of length 0.51 mm (0.020 inch) and the curved labial side has a radius from 0.25 mm (0.010 inch) to 0.38 mm (0.016 inch).

7. An orthodontic arch wire as claimed in any one of claims 1 to 4, wherein the wire occlusal side is of length 0.56 mm (0.022 inch), the lingual side is of length 0.43 mm (0.017 inch) and the curved labial side has a radius from 0.23 mm (0.009 inch) to 0.33 mm (0.013 inch).

* * * * *